United States Patent [19]

Euteneuer et al.

[11] Patent Number: 5,129,887
[45] Date of Patent: Jul. 14, 1992

[54] ADJUSTABLE MANIFOLD FOR DILATATION CATHETER

[75] Inventors: Charles L. Euteneuer, St. Michael; Lloyd K. Willard, Elk River, both of Minn.

[73] Assignee: Scimed Life Systems, Inc., Maple Grove, Minn.

[21] Appl. No.: 630,725

[22] Filed: Dec. 20, 1990

Related U.S. Application Data

[63] Continuation of Ser. No. 280,836, Dec. 7, 1988, abandoned.

[51] Int. Cl.⁵ .............................................. A61M 29/02
[52] U.S. Cl. ....................................... 606/194; 604/96; 604/165; 604/283
[58] Field of Search ................................ 604/93–100, 604/280–283, 905, 101, 165; 606/191–192, 194; 600/17, 18

[56] References Cited

U.S. PATENT DOCUMENTS

| | | | |
|---|---|---|---|
| 4,252,122 | 2/1981 | Halvorsen | 604/164 |
| 4,323,071 | 4/1982 | Simpson et al. | 604/98 |
| 4,362,150 | 12/1982 | Lombardi, Jr. et al. | 600/18 |
| 4,582,181 | 4/1986 | Samson | 128/348.1 |
| 4,637,396 | 1/1987 | Cook | 604/103 |
| 4,641,654 | 2/1987 | Samson et al. | 128/344 |
| 4,646,742 | 3/1987 | Packard et al. | 128/344 |
| 4,669,469 | 6/1987 | Gifford, III et al. | 128/305 |
| 4,730,616 | 3/1988 | Frisbie | 604/164 X |
| 4,838,269 | 6/1989 | Robinson et al. | 128/344 |
| 5,078,727 | 1/1992 | Hannam et al. | 606/194 |

FOREIGN PATENT DOCUMENTS

0086338 8/1983 European Pat. Off. .

*Primary Examiner*—C. Fred Rosenbaum
*Assistant Examiner*—C. Maglione
*Attorney, Agent, or Firm*—Kinney and Lange

[57] ABSTRACT

An improved manifold assembly for a dilatation catheter permits precise adjustment of the effective length of inner and outer members of the catheter during assembly to avoid mismatches in length of the inner and outer members and to avoid the internal stress and distortions caused thereby.

10 Claims, 3 Drawing Sheets

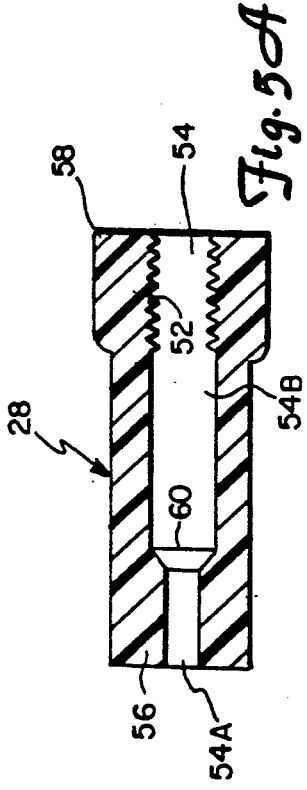
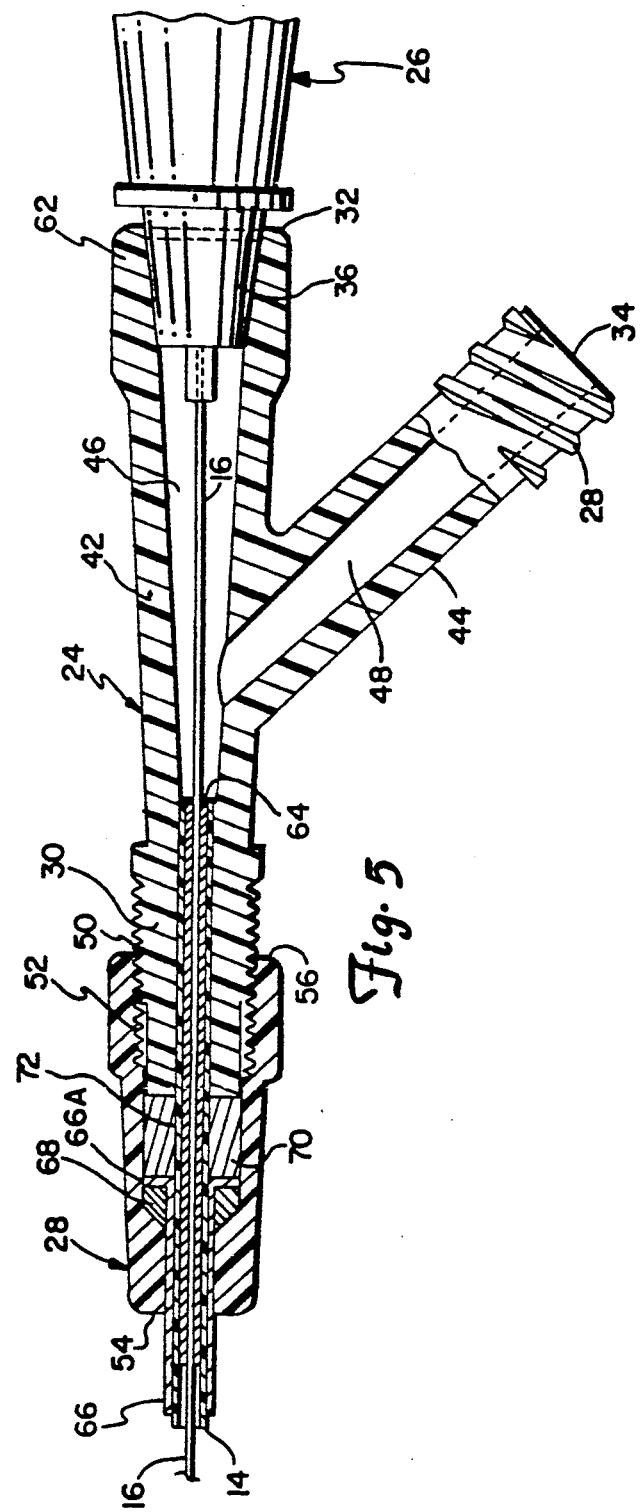

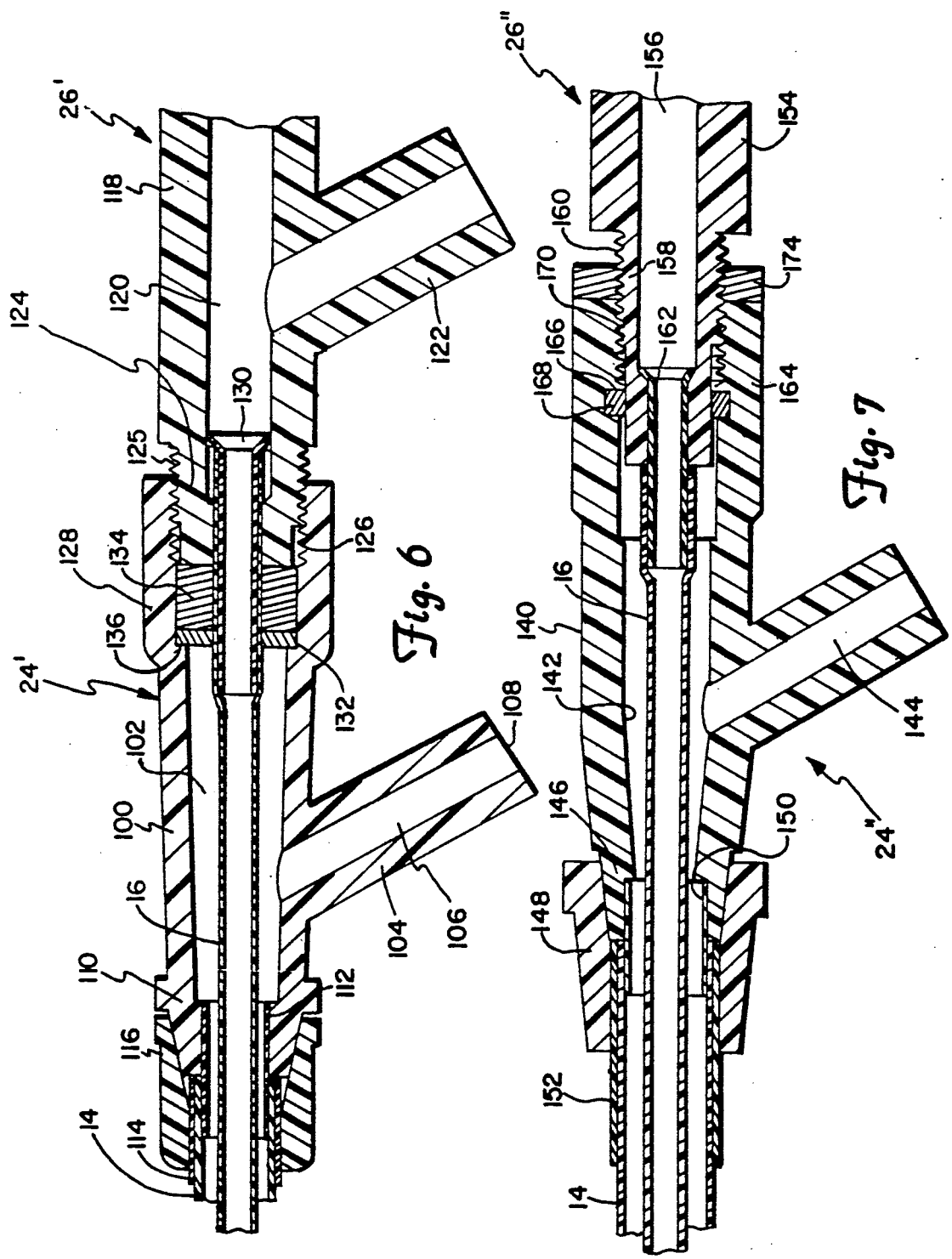

ADJUSTABLE MANIFOLD FOR DILATATION CATHETER

This is a continuation of application Ser. No. 07/280,836, filed Dec. 7, 1988, now abandoned.

BACKGROUND OF THE INVENTION

1. Field of the Invention. angioplasty catheters, and particularly to an adjustable manifold assembly which provides improved efficiency and accuracy in the manufacture of catheter assemblies.

2. Description of the Prior Art.

In the field of angioplasty, specially designed dilatation catheters are used for treating various types of vascular diseases. Angioplasty dilation catheters are available in a number of different sizes and shapes, depending upon the intended use. Some of them, particularly those used for opening of stenoses in the coronary arteries, are very small, and much engineering effort has gone into reducing the size and increasing the flexibility of the tip area of these catheters, while maintaining the strength thereof, to make it easier to advance the catheter through the vascular system and cross a stenosis that is to be dilated.

Various constructon techniques are used for such catheters. One common class of devices is made from an inner tubular member and a coaxial outer tubular member. The inner tubular member extends the length of the catheter and has a central or "thru" lumen designed to receive a guide wire, whereby the catheter can be advanced over a guide wire previously introduced into the patient's vascular system and steered to the site of the stenosis. The outer tubular member is positioned generally coaxially around the inner member and extends substantially the length of the catheter, defining an annular inflation lumen between the two members. An inflatable balloon member is provided at the distal end of the catheter, and is connected with the distal ends of the inner and outer tubular members such that the annular lumen communicates with the interior of the balloon and may be used for inflation and deflation thereof. At the proximal end of the catheter, both the inner and outer tubular members are received and secured in a manifold or handle assembly which is used for manipulation of the catheter and which has suitable fittings for receiving the guide wire and for connection to a controllable source of inflation pressure, as is generally known in the art.

In the manufacture of angioplasty catheters, problems have been encountered in the attachment of the inner and outer tubular members in the manifold assembly. It has been difficult to provide adequate pressure sealing, in view of the fact that the parts are made of thin walled plastic material, and in view of the fact that in use the balloons will be subjected to pressures of over 200 psi. Another problem is that errors or inaccuracies in the lengths of the tubular members or the manner in which they are secured within the manifold assembly have resulted in mismatches in lengths The inner member might be too long or too short with respect to the outer tubular member. Either condition results in a strain or distortion within the catheter, which can cause problems in the tip area thereof, since the tip including the inflatable balloon is the most flexible part of the catheter These strains or distortions can manifest themselves as certain unwanted wrinkles or bends that can interfere with the intended flexibility of the tip, and can even cause an unwanted "set" or preferred flexing direction which can cause problems in advancing the catheter to the site of a stenosis to be treated. Because the inner and outer members may have different moduli, the degree of mismatch, strain and distortion can change between the uninflated and inflated states, further complicating the use of the catheter In many cases it has been necessary to inflate the catheter at the factory for adjustment during assembly to minimize distortions of the tip area in the inflated state.

Because of these problem areas, mass production has been difficult in the prior art, and therefore the usual practice is to custom-build each catheter.

SUMMARY OF THE INVENTION

The manifold assembly of the present invention includes a first member and a second member which are adapted for fitting or attachment together. Both the first member and the second member have passages therethrough for receiving the proximal end of the catheter shaft. A compression seal is provided within the manifold assembly, between the first member and the second member. In a preferred embodiment, the compression seal is an annular resilient member with the catheter shaft passing therethrough. A piece of rigid tubing is positioned inside the catheter shaft generally in the region where the compression seal contacts it Means are provided for adjustably attaching the first and second members such that the spacing there between can be altered to selectively compress the compression seal. This permits precise adjustment of the catheter by manually adjusting the insertion depth of the catheter shaft into the manifold assembly, after which the first and second members are connected to compress the seal which then holds the catheter shaft in place.

BRIEF DESCRIPTION OF THE DRAWINGS

FIG. 5 is a sectional view of the manifold assembly according to a first preferred embodiment of the present invention.

FIG. 5A is a sectional view of the cap of the manifold assembly of FIG. 5.

FIG. 6 is a sectional view of a manifold assembly according to a second preferred embodiment of the invention.

FIG. 7 is a sectional view of another manifold assembly according to a third preferred embodiment of the invention.

DETAILED DESCRIPTION OF THE PREFERRED EMBODIMENTS

Figure 1:
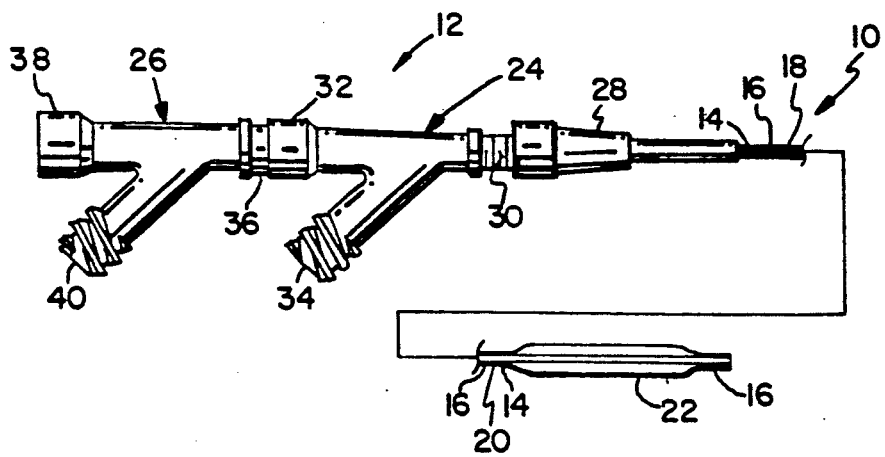
FIG. 1 is a view of a dilatation catheter and its manifold assembly, with a portion of the length of the catheter being broken away.

FIG. 1 shows catheter 10 and its associated manifold assembly 12. Catheter 10 includes an outer tubular member 14 and an inner member 16. Inner member 16 is positioned coaxially within outer member 14, defining an annular inflation lumen 18 therebetween. As illustrated in FIG. 1, inner member 16 is a hollow tube, which defines a thru lumen 20, through which a guide wire (not shown) may pass. Alternatively, inner member 16 may be a solid core wire which extends through outer member 14. The proximal ends of both members 14 and 16 are secured within manifold assembly 12, as is explained in greater detail below. Inner member 16 extends all the way to the distal end of catheter 10. Balloon member 22 is provided at the distal end of catheter 10. The distal end of balloon member 22 is attached to the distal end of inner member 16, and the proximal end of balloon member 22 is attached to the distal end of outer tubular member 14, such that the interior volume of balloon member 22 communicates with annular inflation lumen 18, which is used for controlling the inflation and deflation of balloon member 22. Various techniques are known in the industry for bonding balloon member 22 to members 14 and 16. Alternatively, balloon member 20 may be formed integrally with outer member 14 at the distal end thereof and bonded at its distal end to the distal end of inner member 16.

Manifold assembly 12 includes inflation manifold 24, thru manifold 26 and cap 28. Inflation manifold 24 includes threaded distal end 30, proximal end portion 32 (into which thru manifold 26 is inserted) and inflation/-deflation port 34. Thru manifold 26 includes distal end portion 36 (which is inserted into proximal end portion 32 of inflation manifold 24), proximal thru port 38, and dye port 40.

Figure 2:
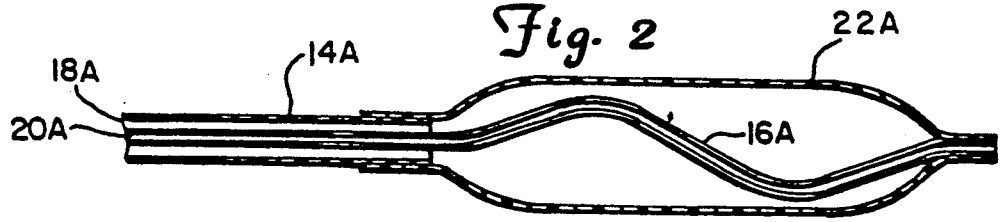
FIG. 2 is a schematic representation of the tip area of a prior art angioplasty catheter illustrating one type of distortion thereof due to internal strain.

Regardless of the specific details of construction of a catheter such as generally described above, certain strains and distortions can be introduced into the distal tip area due to inaccuracies and errors in the manufacturing process, specifically in the joining of the proximal end of the catheter to the manifold assembly. FIG. 2 illustrates one type of distortion that can result in prior art catheters. In the example of FIG. 2, the inner member is indicated by reference number 16A, the outer tubular member by reference number 14A, and the balloon by reference number 22A. Due to the above-noted errors in manufacture or assembly, inner member 16A is too long in relation to outer tubular member 14A. The relative excess length of inner member 16A causes it to form kinks or bends or S-turns in the balloon area, as suggested in FIG. 2 for purposes of illustration. Some of the excess length might be accommodated within the length of the catheter itself, but since outer tubular member 14A is relatively stiffer and the amount of space in lumen 18A between members 14A and 16A is small, most of the excess length will show up in the distal tip area as indicated. Besides creating bulges, this type of strain and distortion also results in a tip area that has different degrees of flexibility in different directions. These effects can cause problems for the cardiologist while trying to manipulate and advance the catheter across a narrow stenosis.

Figure 3:
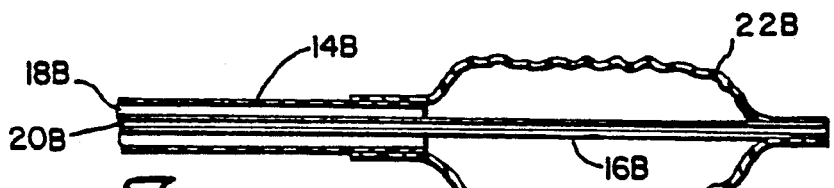
FIG. 3 is a view similar to FIG. 2 of a prior art catheter in an uninflated state illustrating another type of distortion due to strain.

FIG. 3 illustrates the opposite situation, in which inner member 16B is too short in relation to outer tubular member 14B. Since the balloon area is more flexible than outer tubular member 14B, the mismatch is taken up by wrinkling or pleating of the balloon member 22B. This effect, if severe enough, can result in pleats or wrinkles which increase the profile dimension of balloon member 22B as it is being inserted in a tight stenosis.

Figure 4:
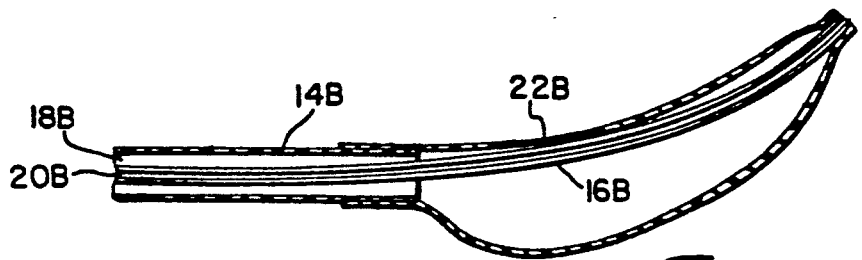
FIG. 4 is a view of the prior art catheter tip of FIG. 3 in an inflated condition illustrating deflection of the tip area.

Another difficulty with the situation of FIG. 3 is illustrated in FIG. 4, where balloon 22B is inflated. This type of mismatch in length causes balloon 22B to inflate in a way that it deflects to a side, in what is referred to as a sausage shape. The direction in which the deflection takes place is not always predictable, and may also interfere with the use of the device.

The errors which lead to the internal strains and distortions indicated in FIG. 2, 3 and 4 can arise in a number of different ways in the manufacturing process. For example, there can be slight errors in the cutting of the lengths of the tubing stock used to form the inner and outer members. Length errors can also occur if the inner and outer members are cut at different times when room temperature differs. There can be slight variances in the positioning of the various elements during the bonding of the balloon to the tube or tubes. Finally, there can be errors in the positioning of the proximal ends of the inner and outer tubular members when they are attached within manifold assembly 12. Some of these steps are done by hand, making absolute control and repeatability difficult. Even a few millimeters of difference in length can lead to the unwanted strains and distortions noted above.

A first preferred embodiment of the improved manifold assembly 12 of the present invention (and especially inflation manifold 24) is illustrated in FIGS. 5 and 5A. Manifold assembly 12, in addition to providing effective pressure sealing, permits precise adjustment of the relative lengths of the inner and outer members 14 and 16 during final assembly so as to completely eliminate the type of strains and distortions discussed above which can occur in prior art catheters.

Manifold assembly 12 includes inflation manifold 24, which is molded from a suitable plastic material. Inflation manifold 24 has a main body 42 of generally elongated cylindrical shape extending from threaded distal end 30 to proximal end 32. Branch 44 is formed integrally with body 42 and extends rearwardly at an angle from approximately the midpoint of body 42. Inflation port 34 is located at the outer end of branch 44, which is threaded to permit connection to an inflation device (not shown).

Body 42 has a central passage 46 extending therethrough from distal end 30 to proximal end 32. Central passage 46 is generally circular in cross section and gradually widens from a relatively narrower diameter at distal end 30, to a wider diameter at proximal end 32. Branch passage 48 extends through branch 44 and connects port 34 with central passage 46.

Threads 50 are formed on the exterior surface of manifold body 42 in the zone near distal end 30 but not extending all the way to the tip of distal end 30. Threads 50 mate with internal threads 52 in the proximal end of cap 28. Cap 28, which is also shown in FIG. 5A, has a central passage 54 therethrough from its distal end 56 to its proximal end 58. Passage 54 includes a relatively narrow section 54A adjacent distal end 56. The central passage 54 widens at angled wall section 60 to a wide section 54B. The rearward portion of wide section 54B contains internal thread 52 which mate with external threads 50 of manifold body 42.

Proximal end 32 of manifold body 42 includes flange portion 62 in which the central passage 46 is flared to receive distal tip 36 of thru manifold 26. In this embodiment, inner member 16 is fixedly attached to thru manifold 26. Adjustment of the relative lengths of inner member 16 and outer member 14 is achieved by adjusting the position of the connection between outer member 14 and inflation manifold 24.

The attachment of catheter 10 to the manifold assembly 12 is as follows. Outer member 14 is received in passage 54 of cap 28 and extends therethrough and into passage 46 in manifold body 42. A length of hollow metallic hypotube 64 is positioned and interference fit within outer member 14 and extends generally through the distal end region 30 of inflation manifold 24, through cap 28 and slightly beyond distal end 56 of cap 28. Strain relief 66 is provided for additional mechanical security in the zone between the catheter 10 and manifold assembly 12. Strain relief 66 takes the form of a piece of plastic tubing having an inside diameter sized to receive outer member 14. A proximal end flange 66A of strain relief 66 is held within the cap 28 between washer 68 and compression seal 70. Washer 68 has a central aperture to receive outer member 14, and a beveled shoulder having an angle corresponding to the angle of wall section 60 of cap 38 to cooperate therewith to secure flange 66A of strain relief 66 between a flat side of washer 68 and compression seal 70.

Seal 70 is a generally cylindrical resilient member having an outside diameter to fit within the wide interior passage 54B of cap 28, and having a central aperture 72 sized to receive outer tubing 14, which extends therethrough. One end of seal 70 abuts against distal end 30 of the inflation manifold 24, and the other end engages flange 66A of strain relief 66 against the flat side of washer 68.

The parts are assembled as indicated in FIG. 5, with cap 28 only loosely threaded onto the inflation manifold 24 initially. Outer member 14 is manually adjusted longitudinally to the proper position after which cap 28 is screwed more tightly onto inflation manifold 24. This causes pressure on compression seal 70 which deforms (radially inwardly) to press outer member 14 against hypotube 64 with sufficient pressure that it is effectively locked in place by frictional forces.

Manifold assembly 12 thus permits fine adjustment of the longitudinal position of outer member 14 within inflation manifold 24 to whatever degree is required for precise assembly of catheter 10 to avoid length mismatches between the inner member 16 and outer member 14 and to avoid the types of internal stress and distortions found in the prior art referred to above. Once the exact positioning has been obtained, tightening of cap 28 secures outer member 14 and prevents further movement.

An alternate embodiment of the invention is illustrated in FIG. 6, in which inflation manifold 24' and thru manifold 26' provide an alternate method for adjustment of the relative lengths of outer and inner members 14 and 16 of catheter 10. In the embodiment shown in FIG. 6, inflation manifold 24' includes a generally elongate manifold body 100 having a central passage 102, and a branch 104 which is used for attachment to an inflation device (not shown). Passage 106 extends through branch 104 from central passage 102 to inflation port 108. At distal end 110 of manifold body 100, a short length of hypotube 112 is molded in place. The outer member 14 and a surrounding strain relief 114 fit over and are bonded to hypotube 112. Cap 116 is secured to distal end 110 of manifold body 100 and helps to hold strain relief tubing 114 in place. Outer member 14, therefore, is fixed with respect to the inflation manifold 24' and the inner member 16 passes freely through hypotube 112 and central passage 102 to be connected at the distal end of thru manifold 26'.

Thru manifold 26' (only a portion of which is shown) includes thru manifold body 118 having a central passage 120 and a branch 122. Distal portion 124 of thru manifold body 118 is of reduced diameter and has external threads 125 which mate with internal threads 126 of proximal portion 128 of inflation manifold body 100.

A piece of hypotube 130 is interference fit in the proximal end of inner member 16, and both extend into central passage 120 of thru manifold 26'. They also pass through central apertures in support washer 132 and cylindrical compression seal 134, which are placed within proximal portion 128 of inflation manifold 24' and are secured between shoulder 136 (which contacts support washer 132) and distal end 124 of thru manifold 26'.

The relative lengths of inner member 16 and outer member 14 can be adjusted by axial movement of inner member 16 and hypotube 130 to the desired position, followed by threading distal portion 124 of thru manifold 26' tightly into proximal portion 128 of inflation manifold 24' so as to compress seal 134, which is then deformed and forced against inner member 16 to hold it mechancially in place and to provide a pressure seal.

The embodiment shown in FIG. 7 operates in a manner similar to that of FIG. 6. In FIG. 7, inflation manifold 24'' has a manifold body 140 with a central passage 142 extending therethrough, and a branch 144. At distal end 146 of manifold 24'' are cap 148 and a molded-in-place hypotube 150. As in the embodiment of FIG. 6, the proximal end of outer member 14 and strain relief tube 152 are secured to hypotube 150 and cap 148 to fix them in position.

Thru manifold 26'' (only a portion of which is shown) has a manifold body 154 with a central passage 156 therethrough, and a distal end portion 158 of reduced diameter which includes external threads 160. Hypotube 162 is fixed in the distal end of central passage 156, which bevels down to a reduced diameter in the distal tip area, and hypotube 162 is flared correspondingly. The proximal end of inner member 16 fits over the outside of the distally protruding portion of hypotube 162 and is bonded thereto.

Proximal end portion 164 of the inflation manifold 24'' includes annular groove 166, which receives and holds resilient annular compression seal 168. Internal passage 142 of inflation manifold body 140 has internal threads 170 located rearwardly of compression seal 168 to receive external threads 160 of thru manifold 26''. The unthreaded section of distal end portion 158 of thru manifold 26'' fits snugly through compession seal 168.

To adjust relative lengths of members 14 and 16 in the embodiment of FIG. 7, thru manifold 26'' can be moved axially with respect to inflation manifold 24'' by means of threads 160 and 170. As thru manifold 26'' is threaded further into or further out from inflation manifold 24'' inner member 16 (which is secured to thru manifold 26'') will be moved relative to the outer member 14, thus effecting the desired relative length adjustment. When the correct position is reached, lock nut 174 is tightened against proximal end portion 164 of inflation manifold 24'' to lock manifolds 24'' and 26'' in position.

It will thus be appreciated that the embodiments of FIG. 6 and 7 also permit fine adjustment of the relative axial positions and effective lengths of the outer and inner members 14 and 16 to whatever degree is required for precise assembly to avoid mismatches and internal stresses and distortions found in the prior art as described above.

Although the present invention has been described with reference to preferred embodiments, workers skilled in the art will recognize that changes may be made in form and detail without departing from the spirit and scope of the invention.

What is claimed is:

1. A catheter system comprising:
    a dilatation catheter having a proximal end and a distal end, the catheter including:
        an inflatable balloon; attached at the distal end and
        a flexible shaft defined by first and second elements which extends proximally from the balloon; and
    a manifold assembly including:
        a cap member having a first passage through which a proximal end portion of the flexible shaft extends;
        a manifold member having a second passage, generally aligned with the first passage, and into which the proximal end portion of the flexible shaft extends;
        means attached to a proximal end of the manifold for receiving the first element of the flexible shaft so as to secure it against movement relative thereof;
        means for connecting the cap member and the manifold member; and
        compression seal means carried by one of the cap and manifold members and having a noncompressed state that allows the second element of the flexible shaft to be moved relative to that member and the first element of the flexible shaft, and a compressed state which provides sufficient frictional force to prevent any relative movement between the second element of the flexible shaft, the first element of the flexible shaft and that member, the compression seal means forming a fluid-tight seal between that member and the flexible shaft of the dilatation catheter.

2. The manifold assembly of claim 1 wherein the means for connecting the cap and manifold members permits spacing between the cap and manifold members to be varied which causes the compression seal means to be compressed from the noncompressed state to the compressed state to force the seal into frictional contact with the second element of the flexible shaft to secure the shaft and prevent relative movement between the shaft and the manifold assembly.

3. The manifold assembly of claim 2 wherein the means for connecting comprises first threads on the cap member and second, mating threads on the manifold member.

4. The manifold assembly of claim 1 wherein the manifold member is an inflation manifold having an inflation port connected to the second passage.

5. The manifold assembly of claim 4 wherein the compression seal means is a generally annular seal carried by the cap member and surrounds the second element of the flexible shaft.

6. The manifold assembly of claim 5 and further comprising:
    a rigid tubing section positioned inside the second element of the flexible shaft generally in a region where the annular seal contacts the second element.

7. A catheter system comprising:
    a dilatation catheter having a proximal end and a distal end, the catheter including:
        an inflatable balloon; and attached at the distal end
        a flexible shaft defined by first and second elements which extends proximally from the balloon; and
    a manifold assembly including:
        an inflation manifold member having a first passage through which a proximal end portion of the flexible shaft extends;
        a thru manifold member having a second passage, generally aligned with the first passage, and into which the proximal end portion of the flexible shaft extends,;
        means for securing a proximal end of the first element of the flexible shaft to the inflation manifold member against movement relative thereto
        means for connecting the inflation manifold member and the thru manifold member; and
        compression seal means carried by one of the inflation and thru manifold members and having a noncompressed state that allows the second element of the flexible shaft to be moved relative to that member and the first element of the flexible shaft, and a compressed state which provides sufficient frictional force to prevent any relative movement between the second element of the flexible shaft, the first element of the flexible shaft and that member, the compression seal means forming a fluid-tight seal between that member and the flexible shaft of the dilatation catheter.

8. The manifold assembly of claim 7 wherein the compression seal means is a generally annular seal positioned between the inflation manifold member and the second element of the flexible shaft.

9. The manifold assembly of claim 8 wherein the means for connecting permits relative longitudinal positions of the inflation and thru manifold members to be varied which causes the annular seal to be compressed from the noncompressed state to the compressed state to force the annular seal into frictional contact with the second element of the flexible shaft.

10. The manifold assembly of claim 9 wherein the means for connecting includes mating threads on a proximal portion of the inflation manifold member and a distal portion of the thru manifold member.

* * * * *

UNITED STATES PATENT AND TRADEMARK OFFICE
CERTIFICATE OF CORRECTION

PATENT NO. : 5,129,887
DATED : July 14, 1992
INVENTOR(S) : CHARLES L. EUTENEUER, LLOYD K. WILLARD It is certified that error appears in the above-identified patent and that said Letters Patent is hereby corrected as shown below:

Col. 7, delete line 10, insert:

"an inflatable balloon attached at the distal end; and"

Col. 8, delete line 12, insert:

"an inflatable balloon attached at the distal end; and"

Signed and Sealed this

Twenty-fifth Day of January, 1994

Attest:

BRUCE LEHMAN

*Attesting Officer*   *Commissioner of Patents and Trademarks*